(12) United States Patent
Zhou et al.

(10) Patent No.: US 7,879,859 B2
(45) Date of Patent: Feb. 1, 2011

(54) DIAGNOSIS AND TREATMENT OF TYPE 2 DIABETES AND OTHER DISORDERS

(75) Inventors: Yun-Ping Zhou, East Bruswick, NJ (US); Jing Li, Skillman, NJ (US); Weizhen Wu, Tenafly, NJ (US); Jin Shang, Short Hils, NJ (US); John R. Thompson, Scotch Plains, NJ (US); Nancy A. Thornberry, Westfield, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 34 days.

(21) Appl. No.: 11/664,381

(22) PCT Filed: Nov. 17, 2006

(86) PCT No.: PCT/US2006/044939

§ 371 (c)(1),
(2), (4) Date: May 10, 2007

(65) Prior Publication Data

US 2009/0131451 A1    May 21, 2009

Related U.S. Application Data

(60) Provisional application No. 60/738,527, filed on Nov. 21, 2005.

(51) Int. Cl.
*A61K 31/50* (2006.01)
*A61K 31/496* (2006.01)
*A61K 31/44* (2006.01)
*A61K 31/415* (2006.01)
*A61K 31/40* (2006.01)

(52) U.S. Cl. .................. 514/252.06; 514/255.05; 514/292; 514/397; 514/411; 514/866

(58) Field of Classification Search ............ 514/252.06, 514/255.05, 292, 397, 411, 866
See application file for complete search history.

(56) References Cited

U.S. PATENT DOCUMENTS 6,586,445 B1    7/2003   Thurieau et al.

6,861,430 B2    3/2005   Troxler et al.

FOREIGN PATENT DOCUMENTS

WO       WO 02/081471 A1    10/2002

OTHER PUBLICATIONS

Poitout, L. et al., "Identification of Potent Non-Peptide Somatostatin Antagonists with sst3 Selectivity" J. Med Chem, vol. 44, pp. 2990-3000, 2001.
Smyth, T.P. et al., "A Substrate Variant as a High-Affinity, Reversible Inhibitor: Insight from the X-ray Structure of Cilastatin Bound to Membrane Dipeptidase" Bioorganic & Medicinal Chemistry, vol. 11, pp. 991-998, 2003.
Benali, N. et al., "Somatostatin Receptors" Diegestion, vol. 62, Suppl 1, pp. 27-32, 2000.
Wang, "SSTR5 ablation in islet results in alterations in glucose homeostasis in mice", FEBS Letters (2005), vol. 579, pp. 3107-3114.
Wang, "Double-gene ablation of SSTR1 and SSTR5 results in hyperinsulinemia . . . ", Surgery (2004), vol. 136, pp. 585-592.
Strowski, "Somatostatin receptor subtype 5 regulates insulin . . . ", Molecular Endocrinology (2003), vol. 17, pp. 93-106.
Strowski, "Somatostatin inhibits insulin and glucagon secretion . . . ", Endocrinology (2000), vol. 141, pp. 111-117.
Ludvigsen, "Expression and distribution of somatostatin receptor subtypes . . . ", J. Histochem. & Cytochem. (2004), vol. 52, pp. 391-400 .
Kumar, "Subtype-selective expression of the five somatostatin receptors . . . ", Diabetes (1999), vol. 48, pp. 77-85.
Koerker, "Somatostatin: Hypothalamic inhibitor of the endocrine pancreas", Science (1974), vol. 184, pp. 482-484.
Efendic, "Effect of somatostatin on glucose induced insulin release . . . ", FEBS Letters (1974), vol. 42, pp. 169-172.
Crider, "Somatostatin receptor agonists and antagonists", Expert Opin. Ther. Patents (2003), vol. 13, pp. 1427-1441.

*Primary Examiner*—Kevin Weddington
(74) *Attorney, Agent, or Firm*—Baerbel R. Brown; Kenrick L. Vidale; John C. Todaro

(57) ABSTRACT

The present application features the use of the somatostatin subtype 3 receptor (SST3) as a target for affecting insulin secretion and for diagnosing diabetes related disorders. Glucose stimulated insulin secretion was found to be stimulated by knocking down expression of SST3 and through the use of a SST3 selective antagonist.

4 Claims, 1 Drawing Sheet

SEQUENCE LISTING

```
<160> NUMBER OF SEQ ID NOS: 17

<210> SEQ ID NO 1
<211> LENGTH: 60
<212> TYPE: DNA
<213> ORGANISM: Artificial Sequence
<220> FEATURE:
<223> OTHER INFORMATION: nucleotide probe

<400> SEQUENCE: 1
tgcaaagggg tgggtgacca gttgagaagt tctttgctgc ttctgacctg agctcctgtc    60

<210> SEQ ID NO 2
<211> LENGTH: 60
<212> TYPE: DNA
<213> ORGANISM: Artificial Sequence
<220> FEATURE:
<223> OTHER INFORMATION: nucleotide probe

<400> SEQUENCE: 2
tttcgctgct tctgacctga gcgcctatca ataaagacag tgactaagaa atttaaaaaa    60

<210> SEQ ID NO 3
<211> LENGTH: 2123
<212> TYPE: DNA
<213> ORGANISM: Artificial Sequence
<220> FEATURE:
<223> OTHER INFORMATION: human sst3 cDNA

<400> SEQUENCE: 3
```

-continued

```
cgcatctctc atcactcccc ctcattctgc ctttcctcct actcacggtc tcctctccct      60
ctccctctct ctctctcccc ctccctcttt tctctctctc tctttctcc acctcctccc      120
gaccccsttt ccctctatt tctattggct tctgtgtccc ttgctcccct cttctcttcc      180
tcaccctggg aagcttctcc ccctatcct tgccctgcc ccccaggat gtgtcctgga       240
gatgggggt gacgtaccag gctctggttg gaagtcagg gccggagacc agatgggaga      300
ggctctgtgg acagccgtgg ccgagggcct gggagggaac ctgagcccgc aagcggtcta    360
gaagtgggtg ccgtgtgggg accctagtta ggagtgccct gggggcacct ggggactggg   420
cagggagagg ggacagcaga atgataacca gcctggcggc aaggagggaa gccctcaccc   480
catgggcagg caaatagctg actgctgacc accctccct cagccatgga catgcttcat    540
ccatcatcgg tgtccacgac ctcagaacct gagaatgcct cctcggcctg gccccagat    600
gccaccctgg caacgtgtc ggcgggccca agcccggcag ggctggccgt cagtggcgtt    660
ctgatccccc tggtctacct ggtggtgtgc gtggtgggcc tgctgggtaa ctcgctggtc   720
atctatgtgg tcctgcggca cacgccagc ccttcagtca ccaacgtcta catcctcaac   780
ctggcgctgg ccgacgagct cttcatgctg gggctgccct cctggccgc ccagaacgcc   840
ctgtcctact ggcccttcgg ctccctcatg tgccgcctgg tcatggcggt ggatggcatc   900
aaccagttca ccagcatatt ctgcctgact gtcatgagcg tggaccgcta cctggccgtg   960
gtacatccca cccgctcggc ccgctggcgc acagctccgg tggcccgcac ggtcagcgcg  1020
gctgtgtggg tggcctcagc cgtggtggtg ctgcccgtgg tggtcttctc gggagtgccc  1080
cgcggcatga gcacctgcca catgcagtgg cccgagccgg cggcggcctg gcgagccggc  1140
ttcatcatct cacggccgc actgggcttc ttcgggccgc tgctggtcat ctgcctctgc  1200
tacctgctca tcgtggtgaa ggtgcgctca gctgggcgcc gggtgtgggc accctcgtgc  1260
cagcggcggc ggcgctccga acgcagggtc acgcgcatgg tggtggccgt ggtggcgctc  1320
ttcgtgctct gctggatgcc cttctacgtg ctcaacatcg tcaacgtggt gtgcccactg  1380
cccgaggagc ctgccttctt tgggctctac ttcctggtgg tggcgctgcc ctatgccaac  1440
agctgtgcca accccatcct ttatggcttc ctctcctacc gcttcaagca gggcttccgc  1500
agggtcctgc tgcggccctc ccgccgtgtg cgcagccagg agcccactgt ggggcccccg  1560
gagaagactg aggaggagga tgaggaggag gaggatgggg aggagagcag ggaggggggc  1620
aaggggaagg agatgaacgg ccgggtcagc cagatcacgc agcctggcac cagcgggcag  1680
gagcggccgc ccagcagagt ggccagcaag gagcagcagc tcctacccca agaggcttcc  1740
actgggagac agtccagcac gatgcgcatc agctacctgt agggcctggg aaagccagg   1800
atggcccgag gaagaggcag aagccgtggg tgtgcctagg gcctacttcc caaggtgcca  1860
caggcccatg atgggatgtt gaggggcctg gactttgatg ctattgctgc caggtcttgc  1920
tgtgtgacct tgggtaggtt gcttctactc tctgggcctt gttttctcct ctgtgactca  1980
gggataggag tcatcagcct ggatgagcta tgtcagatga gaggtttgga gggcactgtt  2040
gctgggctga cctggctgag caggcaaaag gtgggtgcag actggcctcc ccccagggat  2100
ggagtgtctt ggggcatcaa cta                                            2123
```

<210> SEQ ID NO 4
<211> LENGTH: 418
<212> TYPE: PRT
<213> ORGANISM: human

```
<400> SEQUENCE: 4

Met Asp Met Leu His Pro Ser Ser Val Ser Thr Thr Ser Glu Pro Glu
 1               5                  10                  15

Asn Ala Ser Ser Ala Trp Pro Pro Asp Ala Thr Leu Gly Asn Val Ser
            20                  25                  30

Ala Gly Pro Ser Pro Ala Gly Leu Ala Val Ser Gly Val Leu Ile Pro
        35                  40                  45

Leu Val Tyr Leu Val Val Cys Val Val Gly Leu Leu Gly Asn Ser Leu
    50                  55                  60

Val Ile Tyr Val Val Leu Arg His Thr Ala Ser Pro Ser Val Thr Asn
65                  70                  75                  80

Val Tyr Ile Leu Asn Leu Ala Leu Ala Asp Glu Leu Phe Met Leu Gly
                85                  90                  95

Leu Pro Phe Leu Ala Ala Gln Asn Ala Leu Ser Tyr Trp Pro Phe Gly
            100                 105                 110

Ser Leu Met Cys Arg Leu Val Met Ala Val Asp Gly Ile Asn Gln Phe
        115                 120                 125

Thr Ser Ile Phe Cys Leu Thr Val Met Ser Val Asp Arg Tyr Leu Ala
    130                 135                 140

Val Val His Pro Thr Arg Ser Ala Arg Trp Arg Thr Ala Pro Val Ala
145                 150                 155                 160

Arg Thr Val Ser Ala Ala Val Trp Val Ala Ser Ala Val Val Val Leu
                165                 170                 175

Pro Val Val Val Phe Ser Gly Val Pro Arg Gly Met Ser Thr Cys His
            180                 185                 190

Met Gln Trp Pro Glu Pro Ala Ala Ala Trp Arg Ala Gly Phe Ile Ile
        195                 200                 205

Tyr Thr Ala Ala Leu Gly Phe Phe Gly Pro Leu Leu Val Ile Cys Leu
    210                 215                 220

Cys Tyr Leu Leu Ile Val Val Lys Val Arg Ser Ala Gly Arg Arg Val
225                 230                 235                 240

Trp Ala Pro Ser Cys Gln Arg Arg Arg Ser Glu Arg Arg Val Thr
                245                 250                 255

Arg Met Val Val Ala Val Val Ala Leu Phe Val Leu Cys Trp Met Pro
            260                 265                 270

Phe Tyr Val Leu Asn Ile Val Asn Val Val Cys Pro Leu Pro Glu Glu
        275                 280                 285

Pro Ala Phe Phe Gly Leu Tyr Phe Leu Val Val Ala Leu Pro Tyr Ala
    290                 295                 300

Asn Ser Cys Ala Asn Pro Ile Leu Tyr Gly Phe Leu Ser Tyr Arg Phe
305                 310                 315                 320

Lys Gln Gly Phe Arg Arg Val Leu Leu Arg Pro Ser Arg Arg Val Arg
                325                 330                 335

Ser Gln Glu Pro Thr Val Gly Pro Pro Glu Lys Thr Glu Glu Glu Asp
            340                 345                 350

Glu Glu Glu Glu Asp Gly Glu Glu Ser Arg Glu Gly Gly Lys Gly Lys
        355                 360                 365

Glu Met Asn Gly Arg Val Ser Gln Ile Thr Gln Pro Gly Thr Ser Gly
    370                 375                 380

Gln Glu Arg Pro Pro Ser Arg Val Ala Ser Lys Glu Gln Gln Leu Leu
385                 390                 395                 400

Pro Gln Glu Ala Ser Thr Gly Glu Lys Ser Ser Thr Met Arg Ile Ser
                405                 410                 415
```

-continued

Tyr Leu

<210> SEQ ID NO 5
<211> LENGTH: 1287
<212> TYPE: DNA
<213> ORGANISM: Artificial Sequence
<220> FEATURE:
<223> OTHER INFORMATION: mouse sst3 cDNA

<400> SEQUENCE: 5

```
atggccactg ttacctatcc ctcatccgag cctatgacct tggaccctgg gaacacatcc      60
tcgacctggc ccctggatac caccctgggg aacacatccg ctggcgctag cctgacaggc     120
ctggctgtca gtggcatctt gatctctctg gtgtacctgg tggtgtgcgt ggtgggtctg     180
ctgggcaact cgctggtgat ctacgtggtc ctgcggcaca cgtccagccc atcagtgacc     240
agtgtctata tcctcaacct ggctctggct gatgagctct tcatgctagg ctacccttc      300
ctggctgctc agaacgccct gtcctactgg ccctttggat ctctcatgtg ccgtctggtc     360
atggccgtgg atggcatcaa ccagttcacc agcatcttct gcctcaccgt catgagtgtg     420
gaccgctatc tggctgtggt gcaccccaca cgctcagccc gctggcgcac ggcaccagtg     480
gctcgcacgg tcagtcgagc tgtctgggtg gcctcggctg tggtggtgct gcctgtggtt     540
gtgttctcag gagtgccccg gggcatgagc acgtgccaca tgcagtggcc agagccagcg     600
gctgcctggc gaacagcctt tatcatctac atggccgcac tgggcttctt tgggcccctg     660
ctggtcatct gcttgtgcta cttgctcatt gtggtaaagg tgcggtcgac cacccggcgg     720
gtgcgggcgc cctcgtgtca gtgggtacag gcacccgcat gccagcggcg acgccgctct     780
gagcgcaggg tcacacgcat ggtggtggcc gtggtggcac tcttcgtcct ctgctggatg     840
ccttctatc tgctcaacat cgtcaatgtg gtgtgcccgc tgccggagga gcctgccttc     900
ttcggcctct acttcctggt ggtggcgctg ccctatgcca acagctgcgc aaaccccatc     960
ctctacggct tcctctccta ccgcttcaag cagggctttc gcaggatcct gctaagacca    1020
tcacgtcgca ttcggagcca ggagccaggg tcgggacctc cagagaagac tgaagaggag    1080
gaggatgaag aagaagaaga gagaagggaa gaggaggagc ggaggatgca gagagggcag    1140
gagatgaacg ggaggctcag tcagatcgca caggctggca ctagtggaca cagccacgg    1200
ccctgcacag ggactgctaa ggagcagcag cttctgcccc aggaggccac agctggggac    1260
aaggccagca cactgagcca tctgtaa                                        1287
```

<210> SEQ ID NO 6
<211> LENGTH: 428
<212> TYPE: PRT
<213> ORGANISM: mouse

<400> SEQUENCE: 6

Met Ala Thr Val Thr Tyr Pro Ser Ser Glu Pro Met Thr Leu Asp Pro
1               5                   10                  15

Gly Asn Thr Ser Ser Thr Trp Pro Leu Asp Thr Thr Leu Gly Asn Thr
            20                  25                  30

Ser Ala Gly Ala Ser Leu Thr Gly Leu Ala Val Ser Gly Ile Leu Ile
        35                  40                  45

Ser Leu Val Tyr Leu Val Val Cys Val Val Gly Leu Leu Gly Asn Ser
    50                  55                  60

Leu Val Ile Tyr Val Val Leu Arg His Thr Ser Ser Pro Ser Val Thr
65                  70                  75                  80

```
Ser Val Tyr Ile Leu Asn Leu Ala Leu Ala Asp Glu Leu Phe Met Leu
                85                  90                  95
Gly Leu Pro Phe Leu Ala Ala Gln Asn Ala Leu Ser Tyr Trp Pro Phe
            100                 105                 110
Gly Ser Leu Met Cys Arg Leu Val Met Ala Val Asp Gly Ile Asn Gln
            115                 120                 125
Phe Thr Ser Ile Phe Cys Leu Thr Val Met Ser Val Asp Arg Tyr Leu
            130                 135                 140
Ala Val Val His Pro Thr Arg Ser Ala Arg Trp Arg Thr Ala Pro Val
145                 150                 155                 160
Ala Arg Thr Val Ser Arg Ala Val Trp Val Ala Ser Ala Val Val Val
                165                 170                 175
Leu Pro Val Val Val Phe Ser Gly Val Pro Arg Gly Met Ser Thr Cys
            180                 185                 190
His Met Gln Trp Pro Glu Pro Ala Ala Ala Trp Arg Thr Ala Phe Ile
            195                 200                 205
Ile Tyr Met Ala Ala Leu Gly Phe Phe Gly Pro Leu Leu Val Ile Cys
            210                 215                 220
Leu Cys Tyr Leu Leu Ile Val Val Lys Val Arg Ser Thr Thr Arg Arg
225                 230                 235                 240
Val Arg Ala Pro Ser Cys Gln Trp Val Gln Ala Pro Ala Cys Gln Arg
                245                 250                 255
Arg Arg Arg Ser Glu Arg Arg Val Thr Arg Met Val Val Ala Val Val
            260                 265                 270
Ala Leu Phe Val Leu Cys Trp Met Pro Phe Tyr Leu Leu Asn Ile Val
            275                 280                 285
Asn Val Val Cys Pro Leu Pro Glu Glu Pro Ala Phe Phe Gly Leu Tyr
            290                 295                 300
Phe Leu Val Val Ala Leu Pro Tyr Ala Asn Ser Cys Ala Asn Pro Ile
305                 310                 315                 320
Leu Tyr Gly Phe Leu Ser Tyr Arg Phe Lys Gln Gly Phe Arg Arg Ile
                325                 330                 335
Leu Leu Arg Pro Ser Arg Arg Ile Arg Ser Gln Glu Pro Gly Ser Gly
            340                 345                 350
Pro Pro Glu Lys Thr Glu Glu Glu Asp Glu Glu Glu Glu Glu Glu Arg
            355                 360                 365
Arg Glu Glu Glu Arg Arg Met Gln Arg Gly Gln Glu Met Asn Gly
            370                 375                 380
Arg Leu Ser Gln Ile Ala Gln Ala Gly Thr Ser Gly Gln Gln Pro Arg
385                 390                 395                 400
Pro Cys Thr Gly Thr Ala Lys Glu Gln Gln Leu Leu Pro Gln Glu Ala
                405                 410                 415
Thr Ala Gly Asp Lys Ala Ser Thr Leu Ser His Leu
            420                 425

<210> SEQ ID NO 7
<211> LENGTH: 3985
<212> TYPE: DNA
<213> ORGANISM: Artificial Sequence
<220> FEATURE:
<223> OTHER INFORMATION: rat sst3 cDNA

<400> SEQUENCE: 7
caggcgtctc tccttactcc ccctcattct gcctttccgc ccacacactg tctcctctcc     60
```

```
ctctcctctc tctctctcca cctccgaccc tcccoctcct ttccttattt tcctcggcct    120
tcttatgtcc cctgctatct cacatttctg tcatctttgg aagtgccttc tgtcaccccc    180
aactgggtgc catctgaaga cccccatcct gtgtccggca cccgccacgt gtcctggaga    240 tgggggtga cgtatcaggt gcgggtggca agtcaggact gaggaccaga tgggagaggc     300
gacgtgggct gacgtggccc ccgaggacct aggaagggcc caaccaagcc cacaagcact    360
ggaggagtgg gcactgtgtg tcaccccagc tggctgtgct ctggtggtac ctggctgcag    420
aaggttatcc agcctggcga ctgcaaaggg aattcttgcc ctgtgggcag aatcttggaa    480
cctccatgca gcagaatgtc agaactggac caaagagatg caagctaccc atggcttccc    540
aggccttgag caccccctca tgctggcagt ggtgcatctg aagagtccct tccacctttg    600
cagcaacccc gtaaggtttg gctagttgg ctgctgactg atcctcatcc ctgccatggc     660
cgctgttacc tatccttcat ccgtgcctac gaccttggac cctgggaatg catcctcagc    720
ctggcccctg gacacgtccc tgggaatgc atctgctggc actagcctgg caggactggc     780
tgtcagtggc atcttgatct ctctggtgta cctggtggtg tgtgtggtgg gtttgctggg    840
caattcactg gtgatctacg tggttctgcg gcacacgtcc agcccatcag tgaccagtgt    900
ctatatcctc aacctggcac tggctgacga actcttcatg ctggggctac cttttcctggc   960 tgctcagaac gccctgtcct actggccttt cggctctctc atgtgtcgtc tggtcatggc    1020
cgtggatggc atcaaccagt tcaccagcat cttctgcctc accgtcatga gtgtggaccg    1080
ctacctggct gtggtgcacc ccacgcgtc tgcccgctgg cgcacggcac ctgtggctcg     1140
aatggtcagt gcagctgtct gggtggcctc agctgtggtc gtgctgcctg tggttgtgtt    1200
ctcaggagtg ccccgaggga tgagcacgtg ccacatgcag tggccagagc cagcggctgc    1260
ctggcgaaca gccttcatca tctatacggc cgcactgggc ttttttgggc ccctgctggt    1320
catctgctta tgctacctgc ttattgtggt gaaggtgcgg tcgaccacac ggcgggtgcg    1380
ggcgccctcg tgccagtggg tacaggcacc cgcttgccag cggcggcggc gctctgagcg    1440
cagggtgaca cgcatggtgg tggctgtggt ggcactcttc gtcctctgct ggatgccttt    1500
ctatttactc aacatcgtta atgtggtgtg cccgctgccg gaggagcccg ccttctttgg    1560
cctctacttc ctggtggtcg cgctgcccta cgccaacagc tgcgcaaacc ccatcctcta    1620
cggcttcctc tcctaccgct tcaagcaggg cttccgcagg atcctgctaa gaccttctcg    1680
gcgagtacgg agccaggagc cagggtctgg ccctccagag aagacggagg aggaggagga    1740
tgaagaggaa gaagagagaa gggaagagga agagcggagg atgcagagag gcaggagat    1800 gaatgggagg ctcagtcaga tcgcacagcc aggcccagt ggacagcagc aacggccttg     1860
cacagggact gccaaggaac agcagcttct accccaggaa gccacagctg ggacaaggc    1920 cagcacgctg agccatctgt aagaaccttc aaagagccag catgatcctg aagagagcag    1980
aagctatgct tgacctaagg cacgagtacc agacacatgg cagtgttcta agcaagcaac    2040
agctagagtg agcttattta catggctgtc ctggccctct ctggaccgtt gtggtactag    2100
ggtccagtga tggaatgtcc ataggcctgg gctctgtccc actgtgccag gcttgctgt    2160 gtatactttg gccagtcact agccctctct gggtcttgtt ttcttctttt gactcaggga    2220
tgggtaaaat gagccctgtc agaagagggg tctggaatcc ttattgggat taatctccta    2280
atcagagccc aagttaagaa tttgcacagt ctgaccaaga aacaagatat cttggggatc    2340
agtctgtatc ttggccctca aggagataca ccagggcttg ggaaatcaga gatgcagatg    2400
acctgggggt gggtgcttgg ctgaaaccta aaggaagtgt tagttggtgt ggtgggatgc    2460
```

-continued

```
cacggcttag gacgcaagtg agcccttccc atgctgctct gtggcctcag ccactctgtt      2520
catgtgcagg cctcctacct cttctgcagg gcagtccggg tgtcctacag accctcaccc      2580
cagcgtctga gcattgggcc ttctgtgctc ctggacacca ggggaagaac ttcccagaag      2640
gcaggtgaaa ccaagtttca ggggttcttg ctgcttgggc ccccctggga cctacgtgtg      2700
actggtcttc taattttgta ttccttctct ggagggaaga ttgcacacca ccaggctcag      2760
gccacccgga gactgactca ccctattcag gtcagctacc tagtccccag ggctatgcag      2820
cagcctgagg gaaggagagg gagaaaggag gagagggagc tgaggcagta agaagaggag      2880
ggggatggga tcggagggag aagagaacag aactttgtgg tgatcttgag tcaaccttct      2940
cccccttgag ctaagctcag tttgcagcac tgatggtttc aggaaggatc tgaaggagac      3000
atgtgaccag gatcccctgg agggtgcgtg gggctggtga gaggggcaca ggtcatgatg      3060
gagtcgtggg aatgggcttg gctcctcagg agggatggta agtcctttgt gtgggtcagt      3120
cctcccatcc tctattccca gggctccagc tgatgtagag actaacaggc tgtcatgggg      3180
agtagccact gtcccagctg ggtcaggact tcattcttcc cctcccagag atggtccttc      3240
tggtcccagc agtgatggcc ctggaaaggt tgaggcttct gctcaaaccc ccaccctacc      3300
ctgcagaggc agggttctca gggaacccac aaatccagat gttgagaaag ctggatcttc      3360
tattcacctc aagcctcttg gccatacect ctgtctctgc gcctcagtat cctcatcata      3420
gtgagaatgt gatcccccag ttctccagtc tgttagaatc caggagggaa ctgagtcatg      3480
ccaggcaagc tactgctcac cacaatgggg ctgcgtaagg atacaaagcg gccgtgttgt      3540
acctcaggct cagcccacac cttgcccttt aagtgagtgg cttcggtgtc agctactgga      3600
ggtgaaggta ttcatgagaa atggagtgca ggaggtcaga agccaaggac catggagaat      3660
gcaagccacc ccagaaggag gaagtttgca aacataggca tgtatggggc ctgaggccca      3720
gcccaggggt tcctctgaga aggagctggg tcaggaagta agcagtccaa ccttcctgga      3780
tggggtaggt gagccacgtc ttgcaaaggg gtgggtgacc agttgagaag ttctttgctg      3840
cttctgacct gagctcctgt caataaagat agtgactaag aaaaaaaaaa aaaaaaaaa      3900 aaaaaaaaaa aaaaaaaaaa aaaaaaaaaa aaaaaaaaaa aaaaaaaaaa aaaaaaaaaa      3960
aaaaaaaaaa aaaaaaaaaa aaaaa                                            3985
```

<210> SEQ ID NO 8
<211> LENGTH: 428
<212> TYPE: PRT
<213> ORGANISM: rat

<400> SEQUENCE: 8

```
Met Ala Ala Val Thr Tyr Pro Ser Ser Val Pro Thr Thr Leu Asp Pro
 1               5                  10                  15

Gly Asn Ala Ser Ser Ala Trp Pro Leu Asp Thr Ser Leu Gly Asn Ala
            20                  25                  30

Ser Ala Gly Thr Ser Leu Ala Gly Leu Ala Val Ser Gly Ile Leu Ile
        35                  40                  45

Ser Leu Val Tyr Leu Val Val Cys Val Val Gly Leu Leu Gly Asn Ser
    50                  55                  60

Leu Val Ile Tyr Val Val Leu Arg His Thr Ser Ser Pro Ser Val Thr
65                  70                  75                  80

Ser Val Tyr Ile Leu Asn Leu Ala Leu Ala Asp Glu Leu Phe Met Leu
                85                  90                  95
```

```
Gly Leu Pro Phe Leu Ala Ala Gln Asn Ala Leu Ser Tyr Trp Pro Phe
                100                 105                 110

Gly Ser Leu Met Cys Arg Leu Val Met Ala Val Asp Gly Ile Asn Gln
            115                 120                 125

Phe Thr Ser Ile Phe Cys Leu Thr Val Met Ser Val Asp Arg Tyr Leu
        130                 135                 140

Ala Val Val His Pro Thr Arg Ser Ala Arg Trp Arg Thr Ala Pro Val
145                 150                 155                 160

Ala Arg Met Val Ser Ala Ala Val Trp Val Ala Ser Ala Val Val Val
                165                 170                 175

Leu Pro Val Val Val Phe Ser Gly Val Pro Arg Gly Met Ser Thr Cys
            180                 185                 190

His Met Gln Trp Pro Glu Pro Ala Ala Ala Trp Arg Thr Ala Phe Ile
        195                 200                 205

Ile Tyr Thr Ala Ala Leu Gly Phe Phe Gly Pro Leu Leu Val Ile Cys
    210                 215                 220

Leu Cys Tyr Leu Leu Ile Val Val Lys Val Arg Ser Thr Thr Arg Arg
225                 230                 235                 240

Val Arg Ala Pro Ser Cys Gln Trp Val Gln Ala Pro Ala Cys Gln Arg
                245                 250                 255

Arg Arg Arg Ser Glu Arg Arg Val Thr Arg Met Val Val Ala Val Val
            260                 265                 270

Ala Leu Phe Val Leu Cys Trp Met Pro Phe Tyr Leu Leu Asn Ile Val
        275                 280                 285

Asn Val Val Cys Pro Leu Pro Glu Glu Pro Ala Phe Phe Gly Leu Tyr
    290                 295                 300

Phe Leu Val Val Ala Leu Pro Tyr Ala Asn Ser Cys Ala Asn Pro Ile
305                 310                 315                 320

Leu Tyr Gly Phe Leu Ser Tyr Arg Phe Lys Gln Gly Phe Arg Arg Ile
                325                 330                 335

Leu Leu Arg Pro Ser Arg Arg Val Arg Ser Gln Glu Pro Gly Ser Gly
            340                 345                 350

Pro Pro Glu Lys Thr Glu Glu Glu Asp Glu Glu Glu Glu Glu Glu Arg
        355                 360                 365

Arg Glu Glu Glu Arg Arg Met Gln Arg Gly Gln Glu Met Asn Gly
    370                 375                 380

Arg Leu Ser Gln Ile Ala Gln Pro Gly Pro Ser Gly Gln Gln Arg
385                 390                 395                 400

Pro Cys Thr Gly Thr Ala Lys Glu Gln Gln Leu Leu Pro Gln Glu Ala
                405                 410                 415

Thr Ala Gly Asp Lys Ala Ser Thr Leu Ser His Leu
            420                 425

<210> SEQ ID NO 9
<211> LENGTH: 21
<212> TYPE: DNA
<213> ORGANISM: Artificial Sequence
<220> FEATURE:
<223> OTHER INFORMATION: siRNA
<220> FEATURE:
<221> NAME/KEY: misc_feature
<222> LOCATION: (1)...(21)
<223> OTHER INFORMATION: combined DNA/RNA
<220> FEATURE:
<221> NAME/KEY: misc_feature
<222> LOCATION: (1)...(19)
<223> OTHER INFORMATION: RNA
```

```
<400> SEQUENCE: 9
ccuuucggcu cucucaugut t                                                   21

<210> SEQ ID NO 10
<211> LENGTH: 21
<212> TYPE: DNA
<213> ORGANISM: Artificial Sequence
<220> FEATURE:
<223> OTHER INFORMATION: siRNA
<220> FEATURE:
<221> NAME/KEY: misc_feature
<222> LOCATION: (1)...(21)
<223> OTHER INFORMATION: combined DNA/RNA
<220> FEATURE:
<221> NAME/KEY: misc_feature
<222> LOCATION: (1)...(19)
<223> OTHER INFORMATION: RNA

<400> SEQUENCE: 10
ggguuugcug ggcaauucat t                                                   21

<210> SEQ ID NO 11
<211> LENGTH: 21
<212> TYPE: DNA
<213> ORGANISM: Artificial Sequence
<220> FEATURE:
<223> OTHER INFORMATION: siRNA
<220> FEATURE:
<221> NAME/KEY: misc_feature
<222> LOCATION: (1)...(21)
<223> OTHER INFORMATION: combined DNA/RNA
<220> FEATURE:
<221> NAME/KEY: misc_feature
<222> LOCATION: (1)...(19)
<223> OTHER INFORMATION: RNA

<400> SEQUENCE: 11
cugacgaacu cuucaugcut t                                                   21

<210> SEQ ID NO 12
<211> LENGTH: 21
<212> TYPE: DNA
<213> ORGANISM: Artificial Sequence
<220> FEATURE:
<223> OTHER INFORMATION: siRNA
<220> FEATURE:
<221> NAME/KEY: misc_feature
<222> LOCATION: (1)...(21)
<223> OTHER INFORMATION: combined DNA/RNA
<220> FEATURE:
<221> NAME/KEY: misc_feature
<222> LOCATION: (1)...(19)
<223> OTHER INFORMATION: RNA

<400> SEQUENCE: 12
acaugagaga gccgaaaggt t                                                   21

<210> SEQ ID NO 13
<211> LENGTH: 21
<212> TYPE: DNA
<213> ORGANISM: Artificial Sequence
<220> FEATURE:
<223> OTHER INFORMATION: siRNA
<220> FEATURE:
<221> NAME/KEY: misc_feature
<222> LOCATION: (1)...(21)
```

```
<223> OTHER INFORMATION: combined DNA/RNA
<220> FEATURE:
<221> NAME/KEY: misc_feature
<222> LOCATION: (1)...(19)
<223> OTHER INFORMATION: RNA

<400> SEQUENCE: 13
ugaauugccc agcaaaccct t                                              21

<210> SEQ ID NO 14
<211> LENGTH: 21
<212> TYPE: DNA
<213> ORGANISM: Artificial Sequence
<220> FEATURE:
<223> OTHER INFORMATION: siRNA
<220> FEATURE:
<221> NAME/KEY: misc_feature
<222> LOCATION: (1)...(21)
<223> OTHER INFORMATION: combined DNA/RNA
<220> FEATURE:
<221> NAME/KEY: misc_feature
<222> LOCATION: (1)...(19)
<223> OTHER INFORMATION: RNA

<400> SEQUENCE: 14
agcaugaaga guucgucagt t                                              21

<210> SEQ ID NO 15
<211> LENGTH: 24
<212> TYPE: DNA
<213> ORGANISM: Artificial Sequence
<220> FEATURE:
<223> OTHER INFORMATION: primer

<400> SEQUENCE: 15
ctgagccatc tgtaagaacc ttca                                           24

<210> SEQ ID NO 16
<211> LENGTH: 22
<212> TYPE: DNA
<213> ORGANISM: Artificial Sequence
<220> FEATURE:
<223> OTHER INFORMATION: primer

<400> SEQUENCE: 16
cgtgccttag gtcaagcata gc                                             22

<210> SEQ ID NO 17
<211> LENGTH: 27
<212> TYPE: DNA
<213> ORGANISM: Artificial Sequence
<220> FEATURE:
<223> OTHER INFORMATION: probe

<400> SEQUENCE: 17
tctgctctct tcaggatcat gctggct                                        27
```

DIAGNOSIS AND TREATMENT OF TYPE 2 DIABETES AND OTHER DISORDERS

CROSS REFERENCE TO RELATED APPLICATIONS

This application is the National Stage of International Application No. PCT/US2006/044939, filed 17 Nov. 2006, which claims the benefit under 35 U.S.C. 119(e) of U.S. Provisional Application No. 60/738,527, filed 21 Nov. 2005.

BACKGROUND OF THE INVENTION

The references cited in the present application are not admitted to be prior art to the claimed invention.

The inability to properly use or produce insulin can result in different metabolic disorders, such as diabetes and Metabolic syndrome (also called Syndrome X). Insulin is a hormone produced by pancreatic beta cells in the islets of Langerhans. Insulin decreases blood glucose levels, modulates carbohydrate and lipid metabolism, and influences the biosynthesis of protein and RNA.

Diabetes mellitus is a syndrome characterized by hyperglycemia resulting from the impairment of insulin secretion and/or insulin action. Impairment of insulin secretion causes type I diabetes mellitus, also known as juvenile insulin-dependant DM (IDDM) or juvenile-onset diabetes. (Merck Manual Sec. 2, Chapter 13, 2005 online version.)

Impairment of insulin action and insulin secretion results in type 2 diabetes mellitus, also know as non-insulin-dependent mellitus. Type 2 diabetes mellitus is characterized by hyperglycemia and insulin resistance. The hyperglycemia results from both an impaired insulin secretory response to glucose and decreased insulin effectiveness in stimulating skeletal muscle glucose uptake and in restraining hepatic glucose production. The beta cells within the pancreatic islets initially compensate for insulin resistance by increasing insulin output. (Polonsky, *Int. J. Obes. Relat. Metab. Disord.* 24 Suppl 2:S29-31, 2000.)

Eventually, a patient may be become diabetic due to the inability to properly compensate for insulin resistance. In humans, the onset of type 2 diabetes due to insufficient increases (or actual declines) in beta cell mass is apparently due to increased beta cell apoptosis relative to non-diabetic insulin resistant individuals. (Butler et al., *Diabetes* 52:102-110, 2003.)

SUMMARY OF THE INVENTION

The present application features the use of the somatostatin subtype 3 receptor (SST3) as a target for affecting insulin secretion and for diagnosing diabetes related disorders. Glucose stimulated insulin secretion was found to be stimulated by knocking down expression of SST3 and through the use of a SST3 selective antagonist.

Thus, a first aspect of the present invention features a method for stimulating insulin secretion in a patient in need thereof. The method comprises the step of administering to the patient an effective amount of a SST3 antagonist or an agent that reduces expression of SST3.

An SST3 antagonist binds to SST3 and inhibits receptor activity. In the treatment of a patient, the overall degree of inhibition of SST3 receptor activity should be sufficient to provide a useful physiological effect such as increasing insulin secretion leading to a reduction in blood glucose level.

An agent reducing SST3 expression acts at the nucleic acid level to inhibit transcription, translation, or processing of SST3 encoding nucleic acids. Examples of such agents include short inhibitory RNA (siRNA), ribozymes, and antisense nucleic acid. In the treatment of a patient, the overall degree of inhibition should be sufficient to provide a useful physiological effect such as increasing insulin secretion leading to a reduction in blood glucose level.

Another aspect of the present invention features a method of screening for a compound affecting at least one of: insulin secretion or glucose uptake. The method involves: (a) identifying a compound binding to, or inhibiting the activity or expression of SST3; and (b) determining the ability of the compound identified in step (a) to affect at least one of one: insulin secretion or glucose uptake.

The initial identification of a compound binding to, or inhibiting the activity or expression of a SST3, can be performed experimentally or based on known information. Information on the SST3 is available in the scientific literature. Preferably, the compound is initially identified experimentally as inhibiting SST3 activity or expression.

Another aspect of the present invention features a method of determining progression of diabetes. The method involves: (a) using a selective SST3 ligand to measure β-cell mass and (b) determining whether there is a low or a decrease in β-cell mass. A low amount of β-cell mass can be determined with respect to the β-cell mass occurring in the general population. A decrease in β-cell mass can be determined with respect to a particular patient over the course of time.

Reference to open-ended terms such as "comprises" allows for additional elements or steps. Occasionally phrases such as "one or more" are used with or without open-ended terms to highlight the possibility of additional elements or steps.

Unless explicitly stated, reference to terms such as "a" or "an" is not limited to one. For example, "a cell" does not exclude "cells". Occasionally phrases such as one or more are used to highlight the possible presence of a plurality.

Other features and advantages of the present invention are apparent from the additional descriptions provided herein including the different examples. The provided examples illustrate different components and methodology useful in practicing the present invention. The examples do not limit the claimed invention. Based on the present disclosure the skilled artisan can identify and employ other components and methodology useful for practicing the present invention.

DETAILED DESCRIPTION OF THE INVENTION

Figure 1:
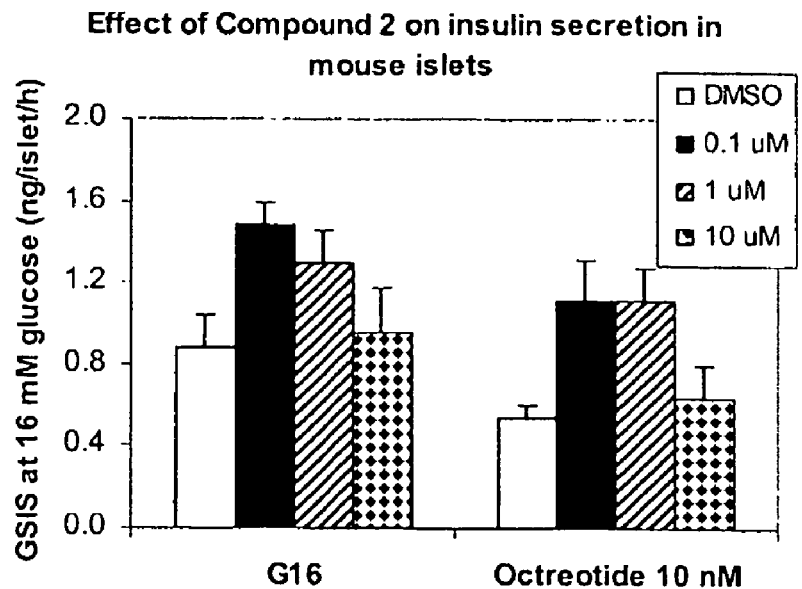
FIG. 1 illustrates the effect of Compound 2 on mouse islets insulin secretion. "G 16" refers to 16 mM glucose. "GSIS" refers to glucose-stimulated insulin secretion.

The SST3 is identified herein as a target for affecting insulin secretion and assessing beta-cell mass. Glucose stimulated insulin secretion was found to be stimulated by knocking down expression of SST3 and through the use of an SST3 selective antagonist. An important physiological action of insulin is to decrease blood glucose levels. Based on the present application, targeting the SST3 has different uses including therapeutic applications, diagnostic applications, and evaluation of potential therapeutics.

I. Somatostin And Somatostin Receptors

Somatostatin is a hormone that exerts a wide spectrum of biological effects mediated by a family of seven transmembrane (TM) domain G-protein-coupled receptors. (Lahlou et al., *Ann. N.Y. Acad. Sci.* 1014:121-131, 2004, Reisine et al., *Endocrine Review* 16:427-442, 1995.) The predominant active forms of somatostatin are somatostatin-14 and somatostatin-28. Somatostatin-14 is a cyclic tetradecapeptide. Somatostatin-28 is an extended form of somatostatin-14.

SST3 is the third, of five, related G-protein receptor subtypes responding to somatostatin. The other receptors are the somatostatin subtype 1 receptor (SST1), somatostatin subtype 2 receptor (SST2), somatostatin subtype 4 receptor (SST4) and somatostatin subtype 5 receptor (SST5). The five distinct subtypes are encoded by separate genes segregated on different chromosomes. (Patel et al., *Neuroendocrinol.* 20:157-198, 1999.) All five receptor subtypes bind somatostatin-14 and somatostatin-28, with low nanomolar affinity. The ligand binding domain for somatostatin is made up of residues in TMs III-VII with a potential contribution by the second extracellular loop. Somatostatin receptors are widely expressed in many tissues, frequently as multiple subtypes that coexist in the same cell.

The five different somatostatin receptors all functionally couple to inhibition of adenylate cyclase by a pertussin-toxin sensitive protein ($G_{\alpha i1-3}$). (Lahlou et al., *Ann. N.Y. Acad. Sci.* 1014:121-131, 2004.) Somatostatin-induced inhibition of peptide secretion results mainly from a decrease in intracellular $Ca^{2+}$.

Among the wide spectrum of somatostatin effects, several biological responses have been identified with different receptor subtypes selectivity. These include growth hormone (GH) secretion mediated by SST2 and SST5, insulin secretion mediated by SST 1 and SST5, glucagon secretion mediated by SST2, and immune responses mediated by SST2. (Patel et al., *Neuroendocrinol.* 20:157-198, 1999; Crider et al., *Expert Opin. Ther. Patents* 13:1427-1441, 2003.)

Different somatostatin receptor sequences from different organisms are well known in the art. (See for example, Reisine et al., *Endocrine Review* 16:427-442, 1995.) Human, rat, and murine SST3 sequences and encoding nucleic acid sequences are provided in SEQ ID NO: 3 (human sst3 cDNA gi|44890055|ref|NM_001051.2| CDS 526:. 1782); SEQ ID NO: 4 (human sst3 AA gi|4557861|ref|NP_01042.1|); SEQ ID NO: 5 (mouse sst3 cDNA gi|66780401|ref|NM_009218.1| CDS 1 ... 1287); SEQ ID NO: 6 (mouse sst3 AA gi|6678041|ref|NP_03244.1|); SEQ ID NO: 7 (rat sst3 cDNA gi|19424167|ref|NM_133522.1| CDS 656 ... 1942); SEQ ID NO: 8 (rat sst3 A gi|19424168|ref|NP_598206.1|).

II. Measuring SST3 Antagonist Activity

SST3 antagonists can be identified using SST3 and nucleic acid encoding for SST3. Suitable assays include detecting compounds competing with a SST3 agonist for binding to SST3 and determining the functional effect of compounds on a SST3 cellular or physiologically relevant activity.

SST3 cellular activities include cAMP inhibition, phospholipase C increase, tyrosine phsophatases increase, eNOS decrease, $K^+$ channel increase, $Na^+/H^+$ exchange decrease, and ERK decrease. (Lablou et al., *Ann. N.Y. Acad. Sci.* 1014: 121-131, 2004.) Functional activity can be determined using cell lines expressing SST3 and determining the effect of a compound on one or more SST3 activity. (Poitout et al., *J. Med. Chem.* 44:29900-3000, 2001; Hocart et al., *J. Med. Chem.* 41:1146-1154, 1998.)

SST3 binding assays can be performed, for example, by labeling somatostatin and determining the ability of a compound to inhibit somatostatin binding. (Poitout et al., *J. Med. Chem.* 44:29900-3000, 2001; Hocart et al., *J. Med. Chem.* 41:1146-1154, 1998.) Additional formats for measuring binding of a compound to a receptor are well-known in the art.

A physiologically relevant activity for SST3 inhibition, identified herein, is stimulating insulin secretion. Stimulation of insulin secretion can be evaluated in vitro or in vivo.

III. SST3 Antagonists

SST3 antagonists can be identified experimentally or based on available information. A variety of different SST3 antagonists are well known in the art. Examples of such antagonists include peptide antagonists, β-carboline derivatives, and a decahydroisoquinoline derivative. (Poitout et al., *J. Med. Chem.* 44:29900-3000, 2001, Hocart et al., *J. Med. Chem.* 41:1146-1154, 1998, Reubi et al., *PNAS* 97:13973-13978, 2000, Bänziger et al., *Tetrahedron: Assymetry* 14:3469-3477, 2003, Crider et al., *Expert Opin. Ther. Patents* 13:1427-1441, 2003, Troxler et al., International Publication No. WO 02/081471, International Publication Date Oct. 17, 2002) The different known SST3 antagonists can be used as starting points for obtaining additional antagonists.

Antagonists can be characterized based on their ability to bind to SST3 (Ki) and effect SST3 activity ($IC_{50}$), and to selectively bind to SST3 and selectively affect SST3 activity. Preferred antagonists strongly and selectively bind to SST3 and inhibit SST3 activity.

In different embodiments concerning SST3 binding, the antagonist has a Ki (nM) less than 100, preferably less than 50, more preferably less than 25 or more preferably less than 10. Ki can be measured as described by Poitout et al., *J. Med. Chem.* 44:29900-3000, 2001 and Example 7 infra.

A selective SST3 antagonist binds SST3 at least 10 times more than is binds SST1, SST2, SST4, and SST5. In different embodiments concerning selective SST3 binding, the antagonist binds to each of SST1, SST2, SST4, and SST5 with a Ki greater than 1000, or preferably greater than 2000 nM and/or binds SST3 at least 40 times, more preferably at least 50 times, more preferably at least 100 times, or more preferably at least 500 times, greater than it binds to SST1, SST2, SST4, and SST5.

In different embodiment concerning SST3 activity, the antagonist has an $IC_{50}$ (nM) less than 500, preferably less than 100, more preferably less than 50, or more preferably less than 10 nM. $IC_{50}$ can be determined by measuring inhibition of somatostatin-14 induced reduction of cAMP accumulation due to forskolin (1 μM) in CHO-K1 cells expressing SST3, as described by Poitout et al., *J. Med. Chem.* 44:29900-3000, 2001.

Preferred antagonists have a preferred or more preferred Ki, a preferred or more preferred $IC_{50}$, and a preferred or more preferred selectivity. More preferred antagonists have a Ki (nM) less than 25; are at least 100 times selective for SST3 compared to SST1, SST2, SST4 and SST5; and have a $IC_{50}$ (nM) less than 10.

In an embodiment, the antagonist is a β-carboline derivative having the structure of Formula I (Troxler et al., International Publication No. WO 02/081471, International Publication Date Oct. 17, 2002):

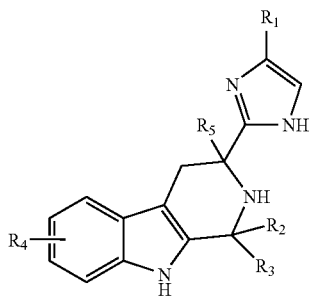

wherein $R_1$ is selected from the group consisting of:

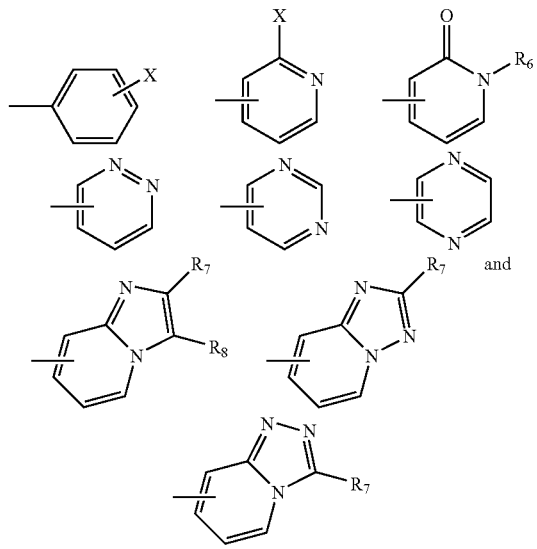

wherein $R_2$ and $R_3$ is each independently selected from the group consisting of: $(C_{1-4})$alkoxy$(C_{1-4})$alkyl, $(C_{3-7})$cycloakyl$(C_{1-4})$alkyl and, if $R_1$ is not an optionally substituted phenyl, $(C_{1-12})$alkyl;

$R_4$ is selected from the group consisting of: hydrogen, $(C_{1-4})$alkyl, $(C_{1-4})$alkoxy, halogen, and trifluoromethyl;

$R_5$ is selected from the group consisting of: hydrogen and $(C_{1-4})$alkyl;

$R_6$ is $(C_{1-4})$alkyl, $R_7$ and $R_8$ is each independently selected from the group consisting of: hydrogen and $(C_{1-4})$alkyl; and X is selected from the group consisting of hydrogen, $(C_{1-4})$alkoxy, $(C_{1-4})$alkylamino, and di$(C_{1-4})$alkylamino, or a pharmaceutically acceptable salt or solvate thereof.

Examples of different Formula I compounds are provided in Troxler et al., International Publication No. WO 02/081471, International Publication Date Oct. 17, 2002. One such example is (R)-1,1-bis-ethoxymethyl-3-(4-phenyl-1H-imidazol-2-yl)-2,3,4,9-tetrahydro-1H-β-carboline.

Included within Formula I are the different optical isomers that may be present at one or more different chiral carbon, racemic mixtures, and tautomeric forms. Each chiral carbon can be independently either R, S, or racemic.

A halogen is selected from the group consisting of fluorine, chlorine, bromine and chlorine. Preferably, the halogen is either fluorine or chlorine.

A pharmaceutically acceptable salt is a salt suitable for administration to a patient. The salt should be non-toxic in the amount employed.

A solvate refers to association with a solvent such as water. Solvate examples include hydrates, hemihydrates, and trihydrates. Reference to solvate include a solvate of a salt.

Another set of examples are imidazolyl tetrahydro-β-carboline derivatives based on the compounds provided in Poitout et al., J. Med. Chem. 44:29900-3000, 2001. The compounds can generically be described by Formula II:

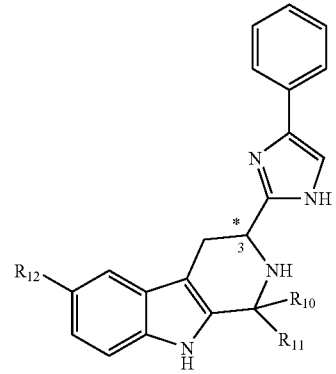

wherein $R_{10}$ is selected from the group consisting of: 4-MeOPh, 4-NMe$_2$Ph, methyl, ethyl, n-butyl, n-pentyl, n-hexyl, and cyclohexyl; $R_{11}$ is independently selected from the group consisting of: hydrogen, ethyl, n-butyl, n-pentyl, n-hexyl, and cyclohexyl; or $R_{10}$ and $R_{11}$ are together 2-adamantyl, 2-indanyl, or 1-acetyl-4-piperidine;

$R_{12}$ is selected from the group consisting of: hydrogen, halogen, methyl and PhCH$_2$O;

or a pharmaceutically acceptable salt or solvate thereof.

Included within Formula II are the different optical isomers that may be present at one or more different chiral carbon, racemic mixtures, and tautomeric forms. Each chiral carbon can be independently either R, S, or racemic.

Examples of Formula II compounds from Poitout et al., J. Med. Chem. 44:29900-3000, 2001 are provided in Table 1.

TABLE 1

Examples of Formula II Compounds

| Compound | $R_{10}$ | $R_{11}$ | $R_{12}$ |
|---|---|---|---|
| 4b | 4-MeOPh | H | H |
| 4c | 4-NMe$_2$Ph | H | H |
| 4e | n-pentyl | H | H |
| 4f | Cyclohexyl | H | H |
| 4g | 2-adamantyl | | H |
| 4h | 2-indanyl | | H |
| 4i | 1-acetyl-4piperidine | | H |
| 4j | Ethyl | ethyl | H |
| 4k | n-butyl | n-butyl | H |
| 4m* | n-butyl | n-butyl | H |
| 4n | n-pentyl | n-pentyl | H |
| 4p | n-hexyl | n-hexyl | H |
| 4q | methyl | cyclohexyl | H |
| 4r** | n-butyl | n-butyl | PhCH$_2$O |
| 4s** | n-butyl | n-butyl | Cl |
| 4t** | n-pentyl | n-pentyl | CH$_3$ |

Unless otherwise indicated, the $C_3$ configuration is R.
*indicates a $C_3$ S configuration.
**indicates a $C_3$ racemic mixture.

Decahydroisoquinoline derivatives can be based on Compound 1 (NVP-ACQ090) (Bänziger et al., *Tetrahedron: Assymetry* 14:3469-3477, 2003):

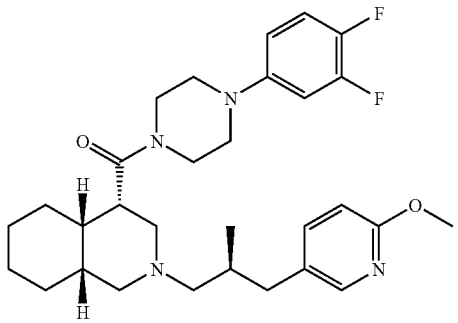

or a pharmaceutically acceptable salt or solvate thereof.

IV. Agents Targeting SST3 Expression

SST3 encoding nucleic acid provides a target for compounds able to hybridize to the nucleic acid. Examples of compounds able to hybridize to a nucleic acid sequence include siRNA, ribozymes, and antisense nucleic acid. The mechanism of inhibition varies depending upon the type of compound. Techniques for producing and using siRNA, ribozymes, and antisense nucleic acid are well known in the art. (E.g., Probst, *Methods* 22:271-281, 2000; Zhang et al., *Methods in Molecular Medicine Vol.* 106. *Antisense Therapeutics* $2^{nd}$ *Edition, p.* 11-34, Edited by I. Philips, Humana Press Inc., Totowa, N.J., 2005.)

Vectors for delivering nucleic acid based compounds include plasmid and viral based vectors. Preferred vectors for therapeutic applications are retroviral and adenovirus based vectors. (Devroe et al., *Expert Opin. Biol. Ther.* 4(3):319-327, 2004, Zhang et al., *Virology* 320:135-143, 2004.)

V. Protein Production

SST3 can be produced using techniques well, known in the art including those involving chemical synthesis and those involving recombinant production. (See e.g., Vincent, *Peptide and Protein Drug Delivery*, New York, N.Y., Decker, 1990; *Current Protocols in Molecular Biology*, John Wiley, 1987-2002, and Sambrook et al., *Molecular Cloning, A Laboratory Manual*, $2^{nd}$ Edition, Cold Spring Harbor Laboratory Press, 1989.)

Recombinant nucleic acid techniques for producing a protein involve introducing, or producing, a recombinant gene encoding the protein in a cell and expressing the protein. A purified protein can be obtained from cell. Alternatively, the activity of the protein in a cell or cell extract can be evaluated.

A recombinant gene contains nucleic acid encoding a protein along with regulatory elements for protein expression. The recombinant gene can be present in a cellular genome or can be part of an expression vector.

The regulatory elements that may be present as part of a recombinant gene include those naturally associated with the protein encoding sequence and exogenous regulatory elements not naturally associated with the protein encoding sequence. Exogenous regulatory elements such as an exogenous promoter can be useful for expressing a recombinant gene in a particular host or increasing the level of expression. Generally, the regulatory elements that are present in a recombinant gene include a transcriptional promoter, a ribosome binding site, a terminator, and an optionally present operator. A preferred element for processing in eukaryotic cells is a polyadenylation signal.

Expression of a recombinant gene in a cell is facilitated through the use of an expression vector. Preferably, an expression vector in addition to a recombinant gene also contains an origin of replication for autonomous replication in a host cell, a selectable marker, a limited number of useful restriction enzyme sites, and a potential for high copy number. Examples of expression vectors are cloning vectors, modified cloning vectors, specifically designed plasmids and viruses.

Due to the degeneracy of the genetic code, a large number of different encoding nucleic acid sequences can be used to code for a particular protein. The degeneracy of the genetic code arises because almost all amino acids are encoded by different combinations of nucleotide triplets or "codons". Amino acids are encoded by codons as follows:

A=Ala=Alanine: codons GCA, GCC, GCG, GCU
C=Cys=Cysteine: codons UGC, UGU
D=Asp=Aspartic acid: codons GAC, GAU
E=Glu=Glutamic acid: codons GAA, GAG
F=Phe=Phenylalanine: codons UUC, UUU
G=Gly=Glycine: codons GGA, GGC, GGG, GGU
H=His=Histidine: codons CAC, CAU
I=Ile=lsoleucine: codons AUA, AUC, AUU
K=Lys=Lysine: codons AAA, AAG
L=Leu=Leucine: codons UUA, UUG, CUA, CUC, CUG, CUU
M=Met=Methionine: codon AUG
N=Asn=Asparagine: codons AAC, AAU
P=Pro=Proline: codons CCA, CCC, CCG, CCU
Q=Gln=Glutamine: codons CAA, CAG
R=Arg=Arginine: codons AGA, AGG, CGA, CGC, CGG, CGU
S=Ser=Serine: codons AGC, AGU, UCA, UCC, UCG, UCU
T=Thr=Threonine: codons ACA, ACC, ACG, ACU
V=Val=Valine: codons GUA, GUC, GUG, GUU
W=Trp=Tryptophan: codon UGG
Y=Tyr=Tyrosine: codons UAC, UAU If desired, expression in a particular host can be enhanced through codon optimization. Codon optimization includes use of more preferred codons. Techniques for codon optimization in different hosts are well known in the art.

VI. Therapeutic Applications

Therapeutic applications of targeting SST3 include treatment of disease or disorders associated with at least one of an insulin deficiency or a hyperglycemic state. Examples of such diseases include hyperglycemia, diabetes and metabolic syndrome. A preferred therapeutic application is treatment of type 2 diabetes in a patient.

Reference to "patient" indicates a mammal capable of contracting a disease or disorder. Preferably, the patient is a human.

VII. Combination Treatment

SST3 antagonists can be used alone or in conjunction with other therapeutic compounds. Available agents that have been used to try to help treat type 2 diabetes include sulfonylureas and related K-ATP channel blockers; glucagon-like peptide 1 (GLP-1) agonists such as GLP-1 and exendin-4; metformin; PPARγ-selective agonists; DP-IV; and insulin. (Inzucchi *JAMA* 287:360-372, 2002; Doyle et al., *Pharmacol Rev.* 55:105-131, 2003; Hoist et al., *Curr. Med. Chem.* 6:1005-1017, 1999; Baggio et al., *Treat. Endocrinol* 1:117-125, 2002; Nauck et al., *Regul. Pept.* 128:135-148, 2005.)

VIII. Compound Preparation And Administration

Compounds can be formulated and administered to a patient using the guidance provided herein along with techniques well known in the art. The preferred route of administration ensures that an effective amount of compound reaches the target. Guidelines for pharmaceutical administration of a therapeutic compound in general are provided in, for example, *Remington's Pharmaceutical Sciences* 20th *Edition*, Ed. Gennaro, Mack Publishing, 2000; and *Modern Pharmaceutics* 2nd *Edition*, Eds. Banker and Rhodes, Marcel Dekicker, Inc., 1990.

Compounds having appropriate functional groups can be prepared as acidic or base salts. Pharmaceutically acceptable salts (in the form of water- or oil-soluble or dispersible products) include conventional non-toxic salts or the quaternary ammonium salts that are formed, e.g., from inorganic or organic acids or bases. Examples of such salts include acid addition salts such as acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate, and undecanoate; and base salts such as ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine and lysine.

Compounds can be administered using different routes including oral, nasal, by injection, transdermal, and transmucosally. Active ingredients to be administered orally as a suspension can be prepared according to techniques well known in the art of pharmaceutical formulation and may contain microcrystalline cellulose for imparting bulk, alginic acid or sodium alginate as a suspending agent, methylcellulose as a viscosity enhancer, and sweeteners/flavoring agents. As immediate release tablets, these compositions may contain microcrystalline cellulose, dicalcium phosphate, starch, magnesium stearate and lactose and/or other excipients, binders, extenders, disintegrants, diluents and lubricants.

When administered by nasal aerosol or inhalation, compositions can be prepared according to techniques well known in the art of pharmaceutical formulation. Such compositions may be prepared for example, as solutions in saline, employing benzyl alcohol or other suitable preservatives, absorption promoters to enhance bioavailability, fluorocarbons, and/or other solubilizing or dispersing agents.

The compounds may also be administered in intravenous (both bolus and infusion), intraperitoneal, subcutaneous, topical with or without occlusion, or intramuscular form. When administered by injection, the injectable solutions or suspensions may be formulated using suitable non-toxic, parenterally-acceptable diluents or solvents, such as Ringer's solution or isotonic sodium chloride solution, or suitable dispersing or wetting and suspending agents, such as sterile, bland, fixed oils, including synthetic mono- or diglycerides, and fatty acids, including oleic acid.

When rectally administered in the form of suppositories, these compositions may be prepared by mixing the drug with a suitable non-irritating excipient, such as cocoa butter, synthetic glyceride esters or polyethylene glycols, which are solid at ordinary temperatures, but liquidify and/or dissolve in the rectal cavity to release the drug.

Suitable dosing regimens for the therapeutic applications can be selected taking into account factors well known in the art including age, weight, sex and medical condition of the patient; the severity of the condition to be treated; the route of administration; the renal and hepatic function of the patient; and the particular compound employed.

Optimal precision in achieving concentrations of drug within the range that yields efficacy without toxicity requires a regimen based on the kinetics of the drug's availability to target sites. This involves a consideration of the distribution, equilibrium, and elimination of a drug. The daily dose for a patient is expected to be between 0.01 and 1,000 mg per adult patient per day.

IX. Diagnostic Applications

A diagnostic application involves determining the progression of diabetes using a SST3 ligand. Radiolabeled SST3 ligands can be used for non-invasive measurement of pancreatic islet, or more specifically, beta-cell mass in patients with type 2 diabetes by either Positron-Emission Tomography (PET) or High-Resolution Magnetic Resonance Imaging (MRI). The same measurement can also be used in type 1 diabetic patients who have received islet transplantation. Preferably, the ligand is a selective SST3 antagonist.

An SST3 ligand binds selectivity to SST3, but need not affect SST3 activity. In different embodiments concerning SST3 binding, the ligand has a Ki (nM) less than 100, preferably less than 50, more preferably less than 25 or more preferably less than 10; and the ligand binds SST3 at least 10 times more than it binds SST1, SST2, SST4, and SST5. In different embodiments concerning selective SST3 binding, the ligand binds to each of SST1, SST2, SST4, and SST5 with a Ki greater than 1000, or preferably greater than 2000 nM and/or binds SST3 at least 40 times, more preferably at least 50, more preferably at least 100 times, and more preferably at least 500 times, greater than it binds to SST1, SST2, SST4, and SST5. In an additional embodiment, the ligand is an SST3 antagonist as described above in Section III supra.

X. EXAMPLES

Examples are provided below to further illustrate different features of the present invention. The examples also illustrate useful methodology for practicing the invention. These examples do not limit the claimed invention.

Example 1

Up-Reputation of SST3 by High Glucose in INS-1 (832/13) Cells

Regulation of the gene encoding SST3 was evaluated by measuring gene expression in INS-1 (832/13) cells. INS-1 (832/13) is a glucose responsive insulinoma β-cell line. (Hohmeier et al., *Diabetes* 49:424-430, 2000.)

INS-1 (832/13) were cultured in RPMI medium with low (2 mM) and high (16 mM) glucose for 24 hours before being collected for RNA extraction. Insulin secretion from the 832/13 INS-1 cell was very low at 2 mM glucose, but is several-fold higher at 16 mM glucose. Each treatment was performed in triplicate (i.e., three experiments on three separate days).

The collected RNA samples were hybridized to oligonucleotide microarrays to identify glucose signature genes. Agilent 60-mer oligo microarray technology, which is a two-channel platform, was used. With this technology, two RNA samples are separately labeled with different fluorescent dyes (Cy5 and Cy3) and are then competitively hybridized on a single array. Dye-swap replicates (fluor-reverse pairs) are produced and averaged to cancel any dye labeling bias resulting in the ratio data values.

In this example, the three 2 mM glucose RNA replicate samples were pooled and used as a common reference pool for all the hybridization. The relative expression of genes in the 16 mM, glucose samples to the 2 mM glucose samples were obtained by comparing the intensities of each of the 16 mM glucose samples to that of the common reference pool. The individual ratio values were then combined using the "replicate combined" feature in the Rosetta Resolver system to generate error-weighted mean ratios with associated p values (a hybrid error model or AHEM).

An Agilent Rat 25k v1.2 Chip A array was used. Of about 23 thousands rat genes represented on this chip, the SST3 gene was represented by one probe (SEQ ID NO: 1). Numerous genes were found to be up-regulated by high glucose (totally 1559 for FC>1.2). The SST3 gene was up-regulated by high glucose with a fold change=1.22, and p-value=0.00157.

Example 2

SST3 Gene Expression is Highly Enriched in Mouse and Rat Islets

The relative expression level of SST3 gene expression in pancreatic islets versus various other tissues was assessed by DNA microarray using a Body-Atlas. The Body-Atlas is a molecular anatomic atlas detailing the expression level of different genes in each tissue or cell-type.

Total RNA samples were extracted from a comprehensive collection of tissues (including the pancreatic islets) for normal C57BL/6 mice and Sprague-Dawley rats and hybridized to microarrays (Mouse TOE 75k v1.0 and Rat 50k v2.1) to generate the mouse and rat islet body atlas data, respectively. In each version of the body-atlas, a reference pool of RNA sample was composed by pooling an equal amount of RNA from 10 different tissues. Samples from each tissue (such as islets) were hybridized against the reference pool to obtain the relative expression of each gene.

On the mouse microarray used to construct the mouse body atlas, the probe (SEQ ID NO: 2), representing sst3, showed high islet enrichment (Table 2). There were 422 genes showing high islet enrichment. The data fields included are the ratios of islets' intensity to the intensity of the species-specific reference pool as well as the absolute hybridization intensities. The Tau values are probe- and array-specific background intensities and represent the intensity at which detection of a transcript achieves 90% confidence.

On the rat body atlas (Rat 50k v2.1) the probe (SEQ ID NO: 1) representing the SST3 gene was also identified as highly enriched in rat islets and the insulinoma INS-1 (832/13) cells (Table 3). About 600 other genes also showed high islet and INS-1 enrichment.

TABLE 2

SST3 Gene Expression Profile in a Mouse Body Atlas

| Expression in Mouse | SEQ ID NO: 2 | | |
| --- | --- | --- | --- |
| | Ratio | Intensity | Tau |
| islets of Langerhans | 25.32 | 82.68 | 0.32 |
| brain, hippocampus | 7.68 | 3.92 | 0.20 |
| brain, telencephalon | 4.09 | 2.14 | 0.15 |
| Pituitary gland | 3.69 | 1.75 | 0.25 |
| spinal cord | 2.09 | 1.67 | 0.23 |

TABLE 2-continued

SST3 Gene Expression Profile in a Mouse Body Atlas

| Expression in Mouse | SEQ ID NO: 2 | | |
| --- | --- | --- | --- |
| | Ratio | Intensity | Tau |
| brain, cerebellum | 3.37 | 1.53 | 0.23 |
| brain, hypothalamus | 3.42 | 1.41 | 0.15 |
| Pancreas | 0.70 | 0.36 | 0.31 |
| Vagina | 0.27 | 0.20 | 0.26 |
| Ovary | 0.34 | 0.18 | 0.30 |
| Stomach | 0.34 | 0.15 | 0.23 |
| muscle, soleus | 0.21 | 0.15 | 0.28 |
| small intestine, jejunum, smooth muscle | 0.24 | 0.15 | 0.27 |
| colon, rectum | 0.38 | 0.14 | 0.17 |
| Salivary gland | 0.17 | 0.13 | 0.32 |
| Prostate | 0.26 | 0.13 | 0.24 |
| lymph node, mesenteric | 0.23 | 0.12 | 0.27 |
| muscle, toes, long extensor | 0.24 | 0.12 | 0.26 |
| Eye | 0.29 | 0.12 | 0.21 |
| Trachea | 0.18 | 0.12 | 0.27 |
| Liver | 0.26 | 0.12 | 0.22 |
| Penis | 0.29 | 0.11 | 0.27 |
| Colon | 0.31 | 0.11 | 0.26 |
| adrenal gland | 0.31 | 0.10 | 0.21 |
| small intestine, ileum, epithelium | 0.26 | 0.10 | 0.20 |
| Tongue | 0.20 | 0.09 | 0.25 |
| Thymus | 0.17 | 0.09 | 0.22 |
| Heart | 0.21 | 0.08 | 0.21 |
| small intestine, ileum, smooth muscle | 0.18 | 0.08 | 0.24 |
| Adipose tissue, white, retroperitoneal | 0.25 | 0.08 | 0.22 |
| muscle, thigh, quadriceps | 0.24 | 0.07 | 0.19 |
| Adipose tissue, brown, interscapular | 0.20 | 0.07 | 0.23 |
| small intestine, jejunum, epithelium | 0.20 | 0.07 | 0.22 |
| Epididymis | 0.14 | 0.07 | 0.22 |
| Testis | 0.15 | 0.06 | 0.26 |
| Kidney | 0.19 | 0.06 | 0.21 |
| Adipose tissue, white, epididymal | 0.21 | 0.06 | 0.22 |
| colon, cecum | 0.21 | 0.06 | 0.23 |
| Gallbladder | 0.15 | 0.06 | 0.22 |
| Spleen | 0.16 | 0.06 | 0.19 |
| Aorta | 0.14 | 0.05 | 0.25 |
| bone marrow | 0.16 | 0.05 | 0.23 |
| seminal vesicle | 0.10 | 0.04 | 0.25 |
| Lung | 0.13 | 0.04 | 0.17 |

TABLE 3

SST3 Gene Expression Profile in a Rat Body Atlas

| Expression in Rat | SEQ ID NO: 1 | | |
| --- | --- | --- | --- |
| | Ratio | Intensity | Tau |
| islets of Langerhans | 11.81 | 3.27 | 0.34 |
| Insulinoma, INS-1 cells | 10.56 | 5.60 | 0.23 |
| brain, cerebellum | 7.54 | 3.18 | 0.22 |
| lymph node, cervical | 6.50 | 3.28 | 0.26 |
| Thymus | 6.03 | 3.53 | 0.22 |
| Spleen | 4.31 | 2.29 | 0.24 |
| brain, forebrain | 2.75 | 1.17 | 0.31 |
| Pituitary gland | 2.23 | 1.04 | 0.26 |
| Tibia | 1.99 | 0.67 | 0.26 |
| brain, hypothalamus | 1.18 | 0.42 | 0.29 |
| Lung | 1.17 | 0.25 | 0.20 |
| bone marrow | 1.15 | 0.50 | 0.26 |
| spinal cord | 1.13 | 0.45 | 0.26 |
| Testis | 0.75 | 0.24 | 0.32 |
| Colon | 0.74 | 0.27 | 0.25 |
| Insulinoma, RIN-m5F cells | 0.73 | 0.25 | 0.30 |
| Mammary gland | 0.65 | 0.13 | 0.23 |
| Adipose tissue, white, epididymal | 0.62 | 0.21 | 0.24 |
| Ovary | 0.61 | 0.24 | 0.26 |
| adrenal gland | 0.58 | 0.25 | 0.27 |
| Epididymis | 0.46 | 0.18 | 0.28 |
| Heart | 0.45 | 0.16 | 0.30 |
| small intestine, jejunum | 0.44 | 0.15 | 0.30 |
| colon, cecum | 0.43 | 0.14 | 0.27 |

TABLE 3-continued

SST3 Gene Expression Profile in a Rat Body Atlas

| Expression in Rat | Ratio | SEQ ID NO: 1 Intensity | Tau |
|---|---|---|---|
| muscle, soleus | 0.41 | 0.13 | 0.23 |
| small intestine, ileum | 0.40 | 0.15 | 0.32 |
| venae cavae | 0.39 | 0.13 | 0.29 |
| Skin | 0.37 | 0.06 | 0.21 |
| small intestine, duodenum | 0.36 | 0.12 | 0.33 |
| Prostate, ventral | 0.35 | 0.13 | 0.26 |
| Aorta | 0.35 | 0.10 | 0.32 |
| Eye | 0.34 | 0.15 | 0.27 |
| muscle, thigh, quadriceps | 0.33 | 0.10 | 0.22 |
| Esophagus | 0.33 | 0.12 | 0.23 |
| thyroid/parathyroid gland | 0.32 | 0.12 | 0.25 |
| Liver | 0.32 | 0.11 | 0.28 |
| Salivary gland | 0.29 | 0.09 | 0.34 |
| dorsal root ganglia | 0.29 | 0.09 | 0.28 |
| Stomach | 0.28 | 0.12 | 0.28 |
| Uterus | 0.28 | 0.11 | 0.25 |
| Kidney | 0.28 | 0.10 | 0.25 |
| Bladder | 0.27 | 0.09 | 0.29 |
| Harderian gland | 0.22 | 0.06 | 0.24 |

Example 3

Detection of SST3 Gene Expression in Human Islets by Fluorescence-Based Real-Time PCR The expression levels of all five somatostatin receptor subtype in human islets from two different donors and 7 non-islet tissues were determined by the Taqman real-time PCR method. Fluorogenic Taqman probes specific for human sst1, sst2, sst3, sst4 and sst5 were purchased from Applied Biosystems (Foster City, Calif., the catalog numbers are Hs0265617_s1, Hs00265624_s1, Hs00265633_s1, Hs00265639_s1 and Hs00265647_s1 respectively). Absolute mRNA levels for the genes of interest were determined by real-time reverse transcription reaction using the ABI PRISM 7900 Sequence Detection System from Applied Biosystems (Foster City, Calif.) through 40 cycles. β-Actin probe was used as reference to determine the relative abundance of the each gene in different tissues.

The Taqman results showed that sst3, along with sst5, are the two most abundant SST expressed genes in two separate human islet samples, and sst4 is not expressed in human islets. SST3 gene expression was also observed brain (Table 4).

TABLE 4

Relative expression level of SSTs in human tissues

|  | SST1 | SST2 | SST3 | SST5 |
|---|---|---|---|---|
| Hs. Islet 2 | 11.7 | 29.6 | 219.0 | 124.0 |
| Hs. Islet 4 | 3.4 | 6.6 | 51.2 | 46.5 |
| Placenta | 0.3 | 0.1 | 0.0 | 0.0 |
| Pancreas | 0.9 | 1.0 | 0.7 | 0.0 |
| Jejunum | 1.7 | 0.7 | 0.2 | 0.0 |
| Liver | 4.4 | 1.0 | 0.1 | 0.0 |
| Sk. muscle | 0.6 | 0.4 | 0.0 | 0.0 |
| Lymph node | 0.1 | 0.3 | 1.4 | 0.0 |
| Brain | 4.2 | 13.0 | 7.0 | 1.0 |

Example 4 siRNA Mediated Gene Knockdown of Genes Whose Expression is Required for Normal Glucose-Stimulated Insulin Secretion RNAi mediated gene knockdown has proven to be useful in elucidating the biological function of different genes. To study the function of candidate target genes in pancreatic beta-cell, we developed a robust method of siRNA mediated gene knockdown that can be used to screen for genes whose expression is required for normal glucose-stimulated insulin secretion (GSIS) function in the rat insulinoma cell line INS-1 (832/13).

Three 21-mer siRNA oligos were designed against each candidate gene and used as a pool at the final concentration of 20 uM. The siRNA oligos were delivered to the cells by Nucleofector Device (Amaxa, Gaithersburg, Md.). The INS-1 (832/13) cells were trypsinized, centrifuged, and resuspended in 100 ul Nucleofector solution V ($2.25 \times 10^6$ cells per reaction). Seven and a half microliters of pooled siRNA were then added to the cell suspension. The cells were electroporated with Amaxa Nucleofector Device program T21. After electroporation, the cells were transferred and split into 9 wells in 96-well plate with 200 ul of regular culture medium (RPMI 1640 with 10% FCS and 11 mM glucose).

GSIS assays were performed after 48 hours. Prior to the assay, cells were washed once with glucose-free Krebs-Ringer Bicarbonate (KRB) medium and cells were incubated with the KRB medium for another 2 hours. The medium were replaced with fresh KRB supplemented with 2, 8, and 16 mM glucose and the cells were incubated for another 2 hours. Supernatants were taken out at the end of incubation for insulin measurement by Ultrasensitive Rat Insulin ELISA kit (ALPCO, Salem, N.H.).

The degree of gene knockdown by the siRNA oligos was quantified by Taqman real-time PCR also at 48 hours after electroporation. The method consistently obtained >70% knockdown of the target genes mRNA. We used PDE3b (phosphodiesterase 3B) and GCK (glucokinase) as two positive controls. As shown in Example 5, Table 6 (infra), compared to control-shocked INS-1 cells (using random sequence siRNA oligos), knocking down PDE3b increased GSIS by 1.5 to 3 fold, consistent with its role in hydrolyzing cAMP, a key positive mediator of GSIS. On the other hand, knocking down the key glycolytic enzyme, glucokinase, generally suppressed GSIS by 30 to 60%.

This method can also be used in other insulin secreting cells lines such as the murine insulinoma cell line MIN6 cells.

Example 5

SiRNA-Mediated Suppression of SST3 Gene Expression Enhances GSIS in INS-1 Cells To study the role of SST3 in GSIS, we designed three pairs of siRNA oligos against rat sst3 (see Table 5 for sequences) and introduced the oligos into the INS-1 832/13 cells by electroporation as described in Example 4 supra.

TABLE 5 siRNA Oligo Sequences Targeting Rat sst3

| siRNA start | Sense Sequence | Antisense Sequence |
| --- | --- | --- |
| 986 | rCrCUUUrCrGrGrCUrCUrCUrCrAUrGUTT (SEQ ID NO: 9) | RArCrAUrGrArGrArGrArGrCrCrGrArArArGrGTT (SEQ ID NO: 12) |
| 829 | RGrGrGUUUrGrCUrGrGrGrCrArAUUrCrATT (SEQ ID NO: 10) | UrGrArAUUrGrCrCrArGrCrArArArCrCrCTT (SEQ ID NO: 13) |
| 924 | RCUrGrArCrGrArArCUrCUUrCrAUrGrCUTT (SEQ ID NO: 11) | RArGrCrAUrGrArArGrArGUUrCrGUrCrArGTT (SEQ ID NO: 14) |

GSIS assays were performed 48 hours after electroporation. The ratios of insulin concentration measured between 8 mM and 2 mM (G8/G2) and 16 mM and 2 mM (G16/G2) glucose treatments are functional readouts for GSIS. These two ratios for each gene were compared to the sample treated with random sequence siRNA oligos. GCK and PDE3b served as functional controls. A ratio of 0.5 represents fifty percent reduction of GSIS, and a ratio of 2 represents one hundred percent increase of GSIS. Sst3 siRNA treated samples showed 2.7 to 4.4 fold enhancements of GSIS. The results from four independent experiments were summarized in the Table 6.

TABLE 6

Normalized fold of stimulation of GSIS

| | si-GCK | | si-PDE3B | | si-SST3 | |
| --- | --- | --- | --- | --- | --- | --- |
| | G8/G2 | G16/G2 | G8/G2 | G16/G2 | G8/G2 | G16/G2 |
| Exp. 1 | 0.5 | 0.5 | Na | na | 2.9 | 4.4 |
| Exp. 2 | 0.5 | 0.4 | 2.2 | 3.2 | 3 | 2.9 |
| Exp. 3 | 0.6 | 0.7 | 2.2 | 1.5 | 3 | 2.7 |
| Exp. 4 | 0.5 | 0.7 | 1.8 | 2.3 | 2.8 | 4.3 |

The degree of sst3 knockdown was also examined 48 hours after siRNA treatment using Taqman real-time PCR. The rat sst3 specific probes were designed using Primer Express Software (Applied Biosystem) based on SEQ ID NO: 7 (Forward Primer: CTGAGCCATCTGTAAGAACCTTCA (SEQ ID NO: 15); Reverse Primer: CGTGCCTTAGGTCAAG-CATAGC (SEQ ID NO: 16); Probe: TCTGCTCTCTTCAG-GATCATGCTGGCT (SEQ ID NO: 17)). We observed about 55-75% reduction of sst3 mRNA in siRNA-treated cells.

Example 6

SST3 Specific Antagonist Enhances GSIS in Isolated Mouse Islets

Pancreatic islets of Langerhans were isolated from the pancreas of normal C57BL/6J mice (Jackson Laboratory, Maine) by collagenase digestion and discontinuous Ficoll gradient separation, a modification of the original method of Lacy and Kostianovsky (Lacy et al., Diabetes 16:35-39, 1967). The islets were cultured overnight in RPMI 1640 medium (11 mM glucose) before GSIS assay.

To measure GSIS, islets were first preincubated for 30 minutes in the Krebs-Ringer bicarbonate (KRB) buffer with 2 mM glucose (in petri dishes). The KRB medium contains 143.5 mM $Na^+$, 5.8 mM $K^+$, 2.5 mM $Ca^{2+}$, 1.2 mM $Mg^{2+}$, 124.1 mM $Cl^-$, 1.2 mM $PO_4^{3-}$, 1.2 mM $SO_4^{2+}$, 25 mM $CO_3^{2-}$, 2 mg/ml bovine serum albumin (pH 7.4). The islets were then transferred to a 96-well plate (one islet/well) and incubated at 37° C. for 60 minutes in 200 µl of KRB buffer with 2 or 16 mM glucose, and other agents to be tested such as octreotide and a SST3 antagonist. (Zhou et al., J. Biol. Chem. 278: 51316-51323, 2003.) Insulin was measured in aliquots of the incubation buffer by ELISA with a commercial kit (ALPCO Diagnostics, Windham, N.H.).

The SST3 specific antagonist (R)-1,1-bis-ethoxymethyl-3-(4-phenyl-1H-imidazol-2-yl)-2,3,4,9-tetrahydro-1H-β-carboline (racemic structure shown below) was used to evaluate the role of SST3 in glucose stimulated insulin secretion from the β-cell. Compound 2 is described in Troxler et al., International Publication No. WO 02/081471, International Publication Date Oct. 17, 2002:

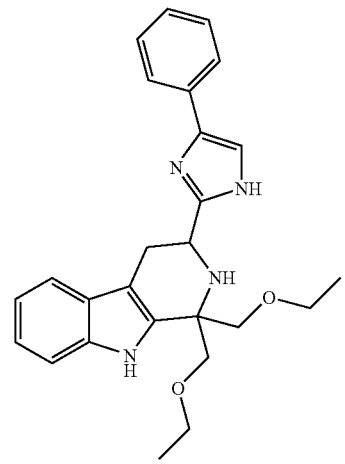

As show in FIG. 1, Compound 2 significantly enhanced GSIS with or without the presence of octreotide (a somatostatin analogue). The enhancement of GSIS was observed at low concentration (0.1 and 1 uM) of the SST3 antagonist. As expected, GSIS was significantly suppressed by 10 nM of Octreotide in isolated islets. The effect of octreotide was fully blocked by 0.1 to 1 uM of Compound 2.

Example 7

Specific Binding of Compound 2 to SST3

The receptor-ligand binding assays of all 5 subtype of SSTRs were performed with membranes isolated from Chinese hamster ovary—(CHO) K1 cells stably expressing the cloned human somatostatin receptors in 96-well format as previous reported. (Yang et al. *PNAS* 95:10836-10841, 1998, Birzin et al. Anal. Biochem. 307:159-166, 2002.)

The stable cell lines for sst1-sst5 were developed by stably transfecting with DNA for all five ssts using Lipofectamine. Neomycin-resistant clones were selected and maintained in medium containing 400 μg/ml G418 (Rohrer et al. *Science* 282:737-740, 1998). Binding assays were performed using (3-$^{125}$I-Tyr11)-SRIF-14 as the radioligand (used at 0.1 nM) and The Packard Unifilter assay plate. The assay buffer consisted of 50 mM Tris HCl (pH 7.8) with 1 mM EGTA, 5 mM MgCl$_2$, leupeptin (10 μg/ml), pepstatin (10 μg/ml), bacitracin (200 μg/ml), and aprotinin (0.5 μg/ml). CHO-K1 cell membranes, radiolabeled somatostatin, and unlabeled test compounds were resuspended or diluted in this assay buffer. Unlabeled test compounds were examined over a range of concentrations from 0.01 nM to 10,000 nM. The Ki values for compounds were determined as described by Cheng and Prusoff *Biochem Pharmacol*. 22:3099-3108, 1973.

As show in Table 7, Compound 2 exhibits very high and specific binding to SST3 ($IC_{50}$=7.8 nM).

TABLE 7

Binding Potencies of Compound 2 on Somatostatin Receptor Subtypes

| Receptor | $IC_{50}$ (nM) |
|---|---|
| SST1 | >1300 |
| SST2 | 150,000 |
| SST3 | 7.8 |
| SST4 | >490 |
| SST5 | >1500 |

Example 8

Figure 2:
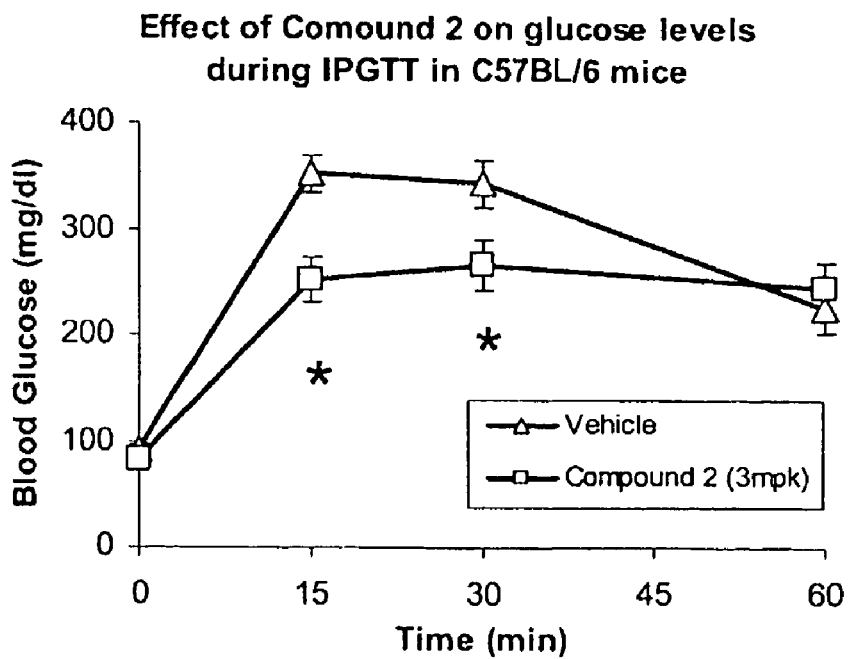
FIG. 2 illustrates the effect of Compound 2 on blood glucose levels during the intraperitoneal glucose tolerance test (IPGTT) in C57BL/6 mice.

SST3 Antagonist Reduces Blood Glucose Levels During Glucose Tolerance Tests in Mice Glucose tolerance tests were performed using an SST3 antagonist in normal C57B1/6 mice. Mice were purchased from Taconic Farm, Inc. (Germantown, N.Y.). Mice were group housed and allowed access to diet and autoclaved water. Mice were fasted for 14 hours prior to glucose tolerance tests. Compound 2 was dosed orally 30 minutes before glucose challenge at 3 mpk [mg drug per kg of body weight]. Control mice were gavaged with same volume of the vehicle (0.25% methylcellulose). At time zero glucose was injected intraperitoneally at the dose of 2 g/kg of body weight. Glucose levels were measured from tail bleeds with a glucometer (Lifescan, Milpitas, Calif.) at specified time points after glucose administration. As shown in FIG. 2, Compound 2 significantly reduced glucose levels during the glucose tolerance test in normal mice.

Other embodiments are within the following claims. While several embodiments have been shown and described, various modifications may be made without departing from the spirit and scope of the present invention.

What is claimed is:

1. A method for increasing insulin secretion in patient in need thereof comprising the step of administering to said patient an effective amount of a somatostatin subtype 3 receptor (SST3) antagonist of Formula 1:

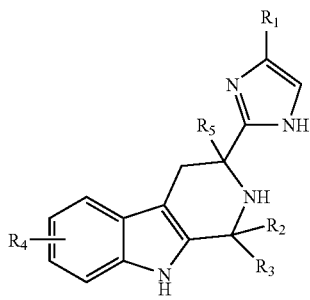

wherein is $R_1$ is selected from the group consisting of:

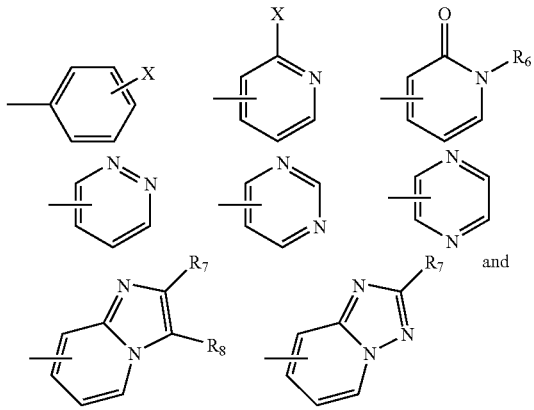

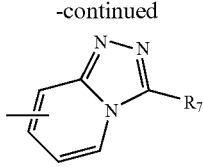

wherein $R_2$ and $R_3$ is each independently selected from the group consisting of: $(C_{1-4})$alkoxy$(C_{1-4})$alkyl, $(C_{3-7})$cycloakyl$(C_{1-4})$alkyl, and, if $R_1$ is not an optionally substituted phenyl, $(C_{1-12})$alkyl;

$R_4$ is selected from the group consisting of: hydrogen, $(C_{1-4})$alkyl, $(C_{1-4})$alkoxy, halogen, and trifluoromethyl;

$R_5$ is selected from the group consisting of: hydrogen and $(C_{1-4})$alkyl;

$R_6$ is $(C_{1-4})$alkyl;

$R_7$ and $R_8$ is each independently selected from the group consisting of: hydrogen and $(C_{1-4})$alkyl; and X is selected from the group consisting of: hydrogen, $(C_{1-4})$alkoxy, $(C_{1-4})$alkylamino, and di$(C_{1-4})$alkylamino;

or a pharmaceutically acceptable salt or solvate thereof.

2. The method of claim 1, wherein said SST3 antagonist is used and said antagonist binds SST3 at least 40 times more than it binds somatostatin subtype 1, 2, 4 and 5 receptor.

3. The method of claim 2, wherein said method reduces blood glucose levels.

4. The method of claim 3, wherein said patient suffers from type 2 diabetes mellitus.

* * * * *